United States Patent
Baram (12)

(10) Patent No.: US 6,734,834 B1
(45) Date of Patent: May 11, 2004

US006734834B1

(54) CLOSED-LOOP AUGMENTED REALITY APPARATUS

(76) Inventor: Yoram Baram, 17 Yakinton Street, Haifa 34792 (IL)

(*) Notice: Subject to any disclaimer, the term of this patent is extended or adjusted under 35 U.S.C. 154(b) by 71 days.

(21) Appl. No.: 09/631,292

(22) Filed: Aug. 2, 2000

Related U.S. Application Data (60) Provisional application No. 60/182,026, filed on Feb. 11, 2000.

(51) Int. Cl.[7] .................... G09G 5/00; G06K 9/62; A61B 5/177

(52) U.S. Cl. ................ 345/8; 345/7; 345/156; 382/155; 600/595

(58) Field of Search ................. 345/7–8, 156, 345/158; 600/595, 415–416; 382/155–156

(56) References Cited

U.S. PATENT DOCUMENTS

| | | | | |
|---|---|---|---|---|
| 4,906,193 A | * | 3/1990 | McMullen et al. | 434/258 |
| 5,597,309 A | | 1/1997 | Riess | |
| 5,722,420 A | * | 3/1998 | Lee | 600/546 |
| 6,005,548 A | * | 12/1999 | Latypov et al. | 345/156 |
| 6,052,114 A | * | 4/2000 | Morifuji | 345/158 |
| 6,176,837 B1 | * | 1/2001 | Foxlin | 600/595 |
| 6,259,889 B1 | * | 7/2001 | LaDue | 434/308 |

OTHER PUBLICATIONS

Reiss, Gait and Parkinson's disease: a conceptual model for an augmented–reality based therapeutic device, Stud Health Technol Inform. 1998 ;58:200–8 (1998).

Widrow, Bernard and Winters, Rodney, "Neural nets for adaptive filtering and adaptive pattern recognition", Computer, Mar. 1988, pp. 25–39.

* cited by examiner

*Primary Examiner*—Regina Liang
*Assistant Examiner*—Duc Q Dinh
(74) *Attorney, Agent, or Firm*—Eitan, Pearl, Latzer & Cohen Zedek, LLP (57) ABSTRACT

Apparatus and system for adaptive augmented reality includes at least one non-radiating sensor, mountable on a body, for detecting body movements and producing signals related to the body movements, and a processor configured to receive the signals and generate an image, wherein the generated image is adapted according to the detected body movements.

The invention provides closed-loop biofeedback for adaptation of body movements, and may be used for treating a movement disorder, such as Parkinson's Disease.

System and method for reducing involuntary movement artifacts from a signal, include a processor for filtering a signal representative of a voluntary movement having involuntary movements therein, an adaptive processor for adaptively filtering a vertical motion signal, and a subtractor for subtracting the involuntary movements from the voluntary movement signal to produce a reduced artifact signal. The adaptive involuntary movement processor adapts its processing using the reduced artifact signal. Method for adaptive augmented reality and for treating a movement disorder includes the steps of providing an image to a person, receiving signals related to movements of the person, adapting the image according to the received signals, and providing the adapted image to the person, wherein the adapted image enables the person to adjust body movements.

39 Claims, 6 Drawing Sheets

| PATIENT | | | DISPLAY OFF | | OPEN-LOOP SYSTEM | | CLOSED-LOOP SYSTEM | | PERCENTAGE CHANGE | |
|---|---|---|---|---|---|---|---|---|---|---|
| NAME AGE | YD | HY | SPEED | STRIDE LENGTH | SPEED | STRIDE LENGTH | SPEED | STRIDE LENGTH | SPEED | STRIDE LENGTH |
| YT 74 | 4 | 2 | 0.884 | 0.465 | 1.063 | 0.541 | 1.107 | 0.571 | 25.3% | 22.9% |
| ST 72 | 2 | 2 | 0.637 | 0.339 | 0.738 | 0.370 | 0.772 | 0.385 | 21.2% | 13.5% |
| JL JL | 1 | 2 | 0.845 | 0.435 | 1.056 | 0.556 | 1.272 | 0.667 | 50.5% | 53.3% |
| MM 67 | 20 | 3 | 0.416 | 0.256 | 0.575 | 0.417 | 0.535 | 0.392 | 28.5% | 52.9% |
| BK 61 | 2 | 2.5 | 0.784 | 0.541 | 0.918 | 0.556 | 0.855 | 0.588 | 9.1% | 8.8% |
| JS 66 | 15 | 4 | 0.314 | 0.168 | 0.073 | 0.111 | 0.339 | 0.220 | 8.0% | 30.7% |
| SM 61 | 15 | 3 | 0.686 | 0.323 | 0.887 | 0.400 | 0.820 | 0.408 | 19.5% | 26.5% |
| MF 76 | 5 | 4 | 0.774 | 0.388 | 1.144 | 0.488 | 0.907 | 0.426 | 17.2% | 9.6% |
| YN 73 | 11 | 3 | 0.695 | 0.406 | 0.881 | 0.444 | 0.791 | 0.417 | 13.8% | 2.1% |
| ES 57 | 3 | 2 | 0.620 | 0.385 | 0.907 | 0.500 | 0.887 | 0.488 | 43.0% | 26.8% |
| MR 73 | 10 | 3 | 1.038 | 0.555 | 0.855 | 0.476 | 0.888 | 0.500 | -14.5% | -9.9% |
| AR 82 | 20 | 4 | 0.508 | 0.339 | 0.601 | 2.000 | 0.590 | 0.385 | 16.0% | 13.5% |
| JJ 59 | 10 | 4 | 0.773 | 0.435 | 0.864 | 0.488 | 0.895 | 0.488 | 15.9% | 12.2% |
| NM 57 | 13 | 4 | 0.403 | 0.154 | 0.243 | 0.140 | 0.668 | 0.351 | 65.5% | 12.8% |
| MEAN 68.2 | 9.36 | 3.04 | 0.642 | 0.357 | 0.765 | 0.539 | 0.803 | 0.445 | 25.7% | 30.8% |
| STD 8.17 | 6.64 | 0.84 | 0.181 | 0.112 | 0.318 | 0.462 | 0.241 | 0.116 | 17.2% | 33.2% |

FIG.7

CLOSED-LOOP AUGMENTED REALITY APPARATUS

This application claims the benefit of Provisional Application No. 60/182,026 filed Feb. 11, 2000.

SUMMARY OF THE INVENTION

There is provided, in accordance width an embodiment of the present invention, an apparatus for adaptive image generation. The apparatus includes at least one non-radiating sensor, mountable on a body, for detecting body movements and producing signals related to the body movements, and a processor configured to receive the signals and generate an image, wherein the generated image is adapted according to the detected body movements.

The processor may include a filtering unit for filtering noise from the received signals, the unit having an adaptive filtering element, and an image generator for providing the generated and adapted images from the filtered and received signals. The filtering unit may include linear elements and non-linear elements, and may be a neural network.

In one embodiment, the non-radiating sensor is an accelerometer. There may be two sensors for producing signals related to movement of a head and body. The generated image may include a geometric pattern, such as a tiled floor or parallel stripes, or it may include a view from real life.

There is also provided, in accordance with an alternative embodiment of the present invention, an apparatus for augmented reality, which includes at least one sensor mountable on at least one part of a body for producing signals from movements of a body part, and a processor for adapting an augmented image based only on the produced signals.

There is also provided, in accordance with an alternative embodiment of the present invention, a system for adaptive augmented or virtual reality which includes at least one non-radiating sensor, mountable on at least one part of a body, for detecting body movements and producing signals related to the body movements, a processor configured to receive the signals and generate an image which is adapted according to the detected body movements, and a display for displaying the generated and adapted images. The system provides closed-loop biofeedback for adaptation of body movements.

There is also provided, in accordance with an alternative embodiment of the present invention, an apparatus for treating a movement disorder. The apparatus includes at least one sensor, mountable on a body, for detecting body movements and producing signals related to the body movements, and a processor configured to receive the signals and generate an image, wherein the generated image is adapted according to the detected body movements.

There is also provided, in accordance with an alternative embodiment of the present invention, a system and method for reducing involuntary movement artifacts from a signal, including a voluntary movement processor for filtering a voluntary movement signal representative of a voluntary movement having involuntary movements therein, an adaptive involuntary movement processor for adaptively filtering a vertical motion signal, and a subtractor for subtracting the involuntary movements from the voluntary movement signal to produce a reduced artifact signal. The adaptive involuntary movement processor adapts its processing using the reduced artifact signal.

Involuntary movement may include tremor or other unwanted movements. Voluntary movement may include walking or other full body movements such as turning, running, etc.

There is also provided, in accordance with an alternative embodiment of the present invention, a method for interaction of an image with body movement, including the steps of providing an image to a person, receiving signals related to movements of the person, adapting the image according to the received signals, and providing the adapted image to the person, wherein the adapted image enables the person to adjust body movements.

The steps may be performed repeatedly so as to provide continuous assistance of body movement. The image may be virtual or augmented. Interaction may include therapy, recreational activities (sports, sex, etc.) or physical assistance.

There is also provided, in accordance with an alternative embodiment of the present invention, a method for treating a movement disorder, including the steps of providing an image to a person, receiving at least one signal from the person, filtering unwanted noise from the signal, adapting the image based on the received and filtered signal, and providing the adapted image to the person, wherein the adapted image enables the person to adjust body movements.

There may be, for example, two signals received from the person—one from the head and one from the body. The step of filtering may be accomplished using a filtering unit having an adaptive filtering element. The method may also include the step of measuring a walking parameter.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

The proposed invention creates an adaptive augmented reality of motion over a virtual image, such as a tiled floor. The system is portable, and can be used for a variety of therapeutic, healing, assistive, or recreational activities. It uses non-radiating sensors, such as accelerometers, which directly measure movements of the body. It is particularly useful for treating diseases with motion impairment, such as Parkinson's Disease (PD), by providing closed-loop biofeedback for gait initiation, sustainment and stabilization.

Figure 1A:
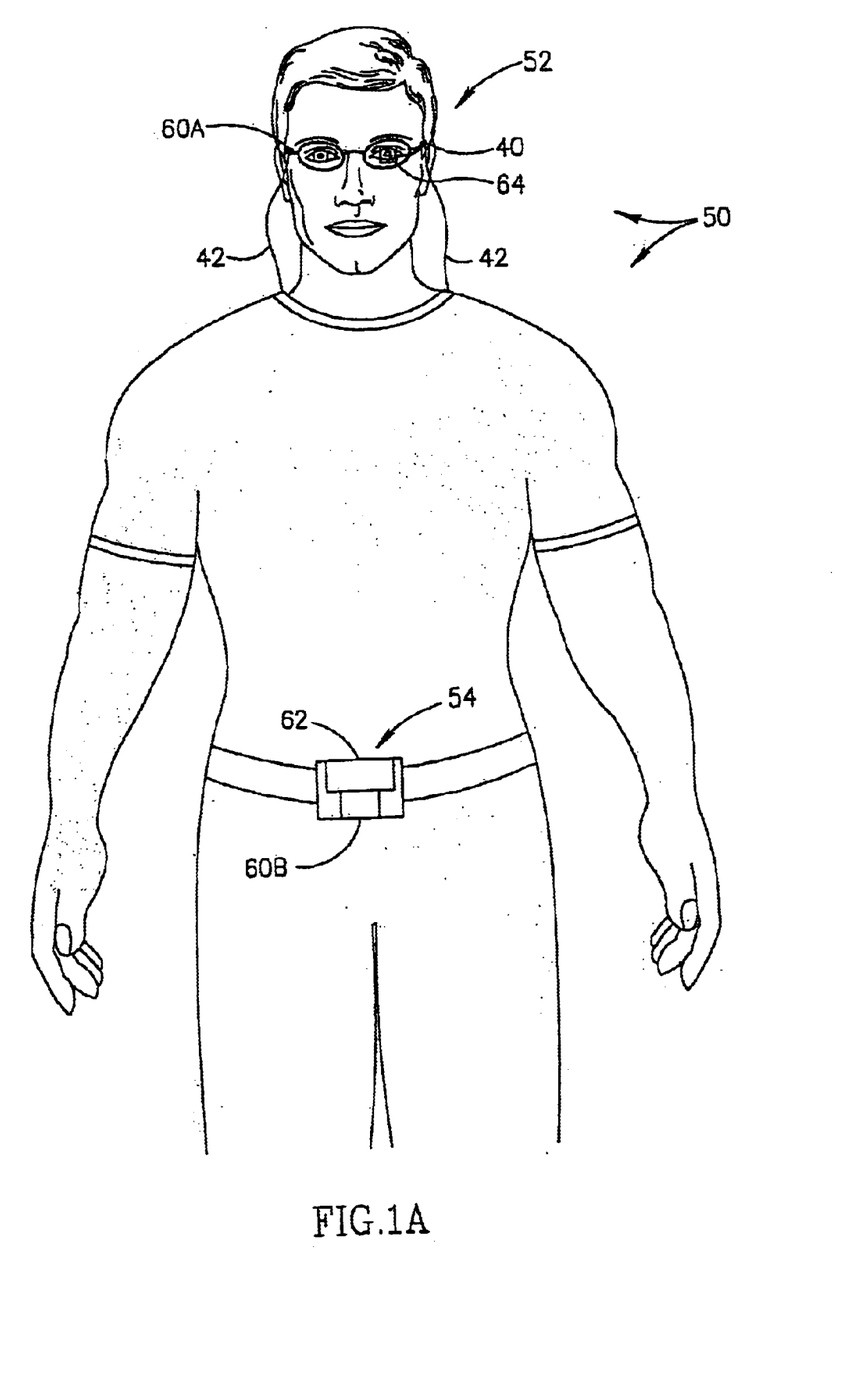
FIGS. 1A and 1B are schematic illustrations of a user wearing one embodiment of the present invention.
Figure 1B:
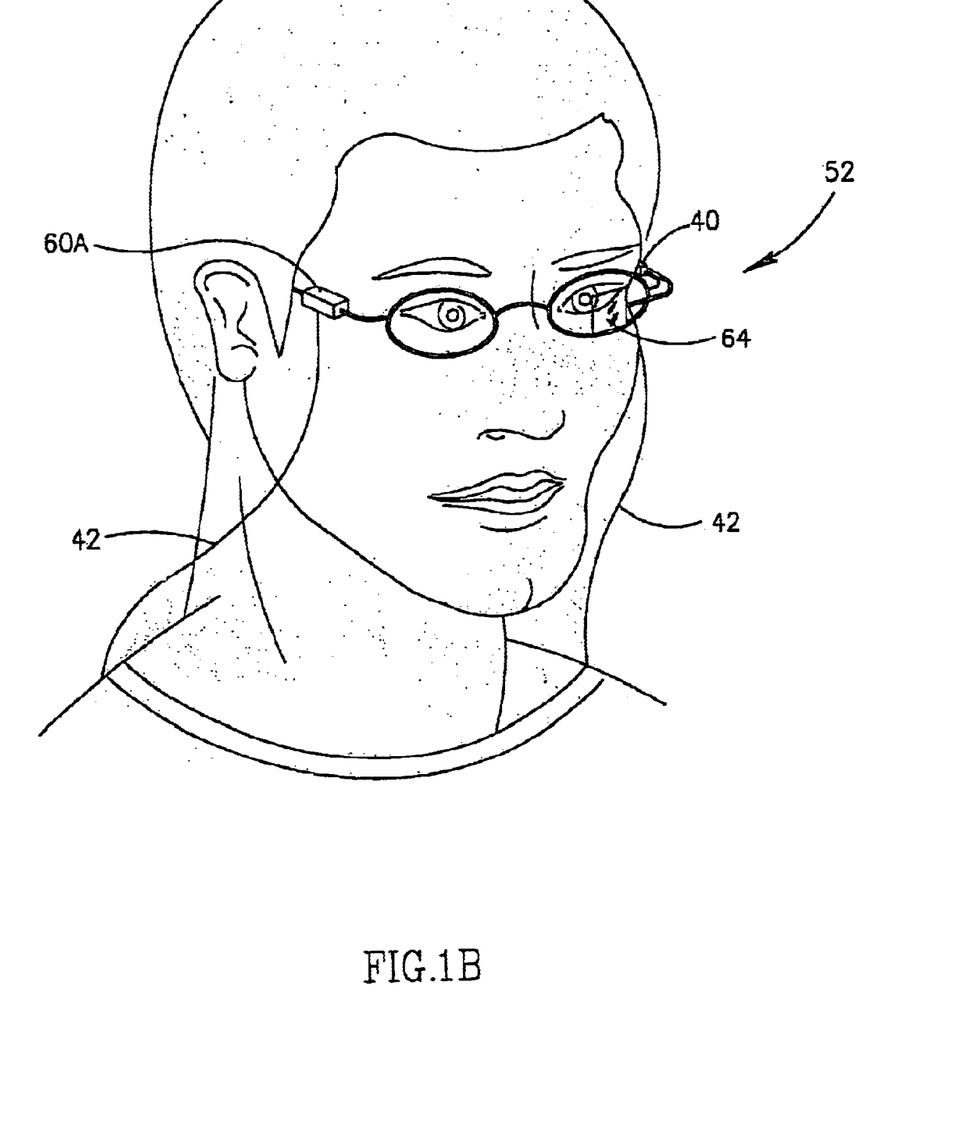

Reference is now made to FIGS. 1A and 1B, which illustrate one embodiment of the system on a user's body. FIG. 1A shows an overview of the entire system, and FIG. 1B shows a detailed view of a portion of the system. The adaptive augmented reality apparatus, generally referenced 50, is portable and generally self-contained, and comprises a head-mounted assembly 52 and a body-mounted assembly 54. Head-mounted assembly 52, comprising a sensor 60A and a display 64, is attached to a pair of glasses 40. Glasses 40 may be standard eyeglasses, with display 64 and sensor 60A attached by, for example, clips. Sensors 60A and 60B are non-radiating sensors, such as accelerometers. Other types of non-radiating sensors may be used as well.

Display 64 overlays a portion of one lens of glasses 40, protruding out approximately 1 cm past the lens plane, as shown in FIG. 1B. Display 64 is a small (for example, 1 cm×1 cm) piece, situated directly in front of one eye 41. In this way, display 64 is close enough to eye 41 to allow the user to see a full view image on display 64 without obscuring any view of the surroundings. Display 64 may be, for example, a liquid crystal display (LCD).

Alternatively, integrated eyeglasses may be used, where display 64 is already incorporated within glasses 40. Such integrated glasses are available from, for example, i-glasses LC Model #500881, i-O Display Systems, LLC, Menlo Park, Calif., USA; or The MicroOptical Corporation, Westwood, Mass., USA Display 64, whether located internally or externally to glasses 40, is equipped with VGA or video connectors (not shown).

Sensor 60A is, for example, a tilt sensor such as Model# CXTILT02E or Model # CXTA02, available from Crossbow Technology, Inc., San Jose, Calif., USA, used to measure tilt of the head with respect to the vertical. Alternatively, sensor 60A may be a sensor that can detect other movements as well as head tilt, such as a 3-axis accelerometer.

Head-mounted assembly 52 is connected to bodymounted assembly 54 by wires 42, as shown in FIG. 1A. Alternatively, wireless connection is possible as well. Bodymounted assembly 54 comprises a processor 62 and a 3-axis accelerometer 60B, for example, translational accelerometer Model # CXL04M3 (Crossbow Technology, Inc., San Jose, Calif., USA).

Body-mounted assembly 54 may be configured in a box of a reasonable size for a person to wear, for example, but not limited to, one having dimensions 7×12×3 cm. Bodymounted assembly 54 is preferably attached to a belt, but may be connected to the body in any number of ways such as by a chest strap, adhesive, or other connecting device.

Figure 2A:
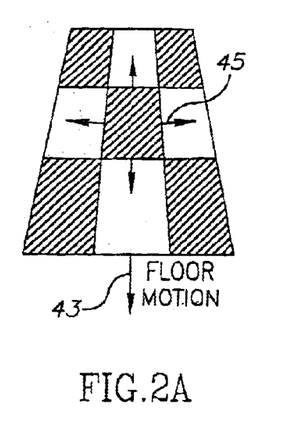
FIGS. 2A and 2B are illustrations of images viewed by the user of FIGS. 1A and 1B.
Figure 2B:
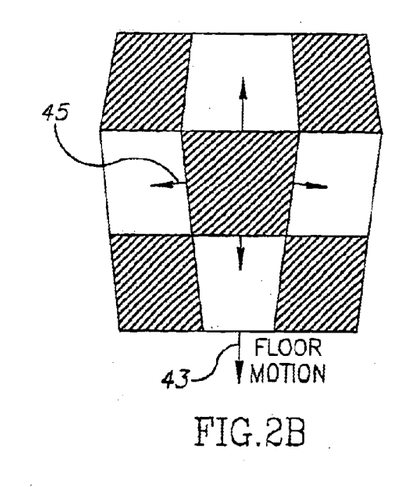

Reference is now made to FIGS. 2A and 2B, which show examples of images viewed by the user while wearing system 60. The image displayed in FIG. 2A is adapted during movement and shown in FIG. 2B. FIG. 2A shows a virtual tiled floor image as displayed to the user during normal walk. The floor moves as the user walks, in an opposite direction as depicted by arrow 43, to simulate a real floor as it appears to someone walking. If the user stumbles or falls forward, an image such as the one shown in FIG. 2B is displayed to the user, to simulate the actual view of a real tiled floor during stumble or fall. The image is continuously adapted to the motions of the user to create more realistic dynamics of the virtual world viewed by the patient. Consequently, the virtual floor viewed by the user moves only during actual motion, at a rate equal to this motion, as in real life. This enables the user to walk at his or her own pace, which may be variable and governed by individual motion characteristics.

Thus, the tiles as shown in FIG. 2B expand as the user looks down or stumbles, and contract as he picks up his head and looks farther away, as in real life. Inner arrows 45 indicate directions of movement of the edges of the tiles in response to the falling motion. Thus, the floor expands while still in motion. Furthermore, as the user turns around, the image turns in the other direction, as in real life. This feature is of particular importance for PD patients since a high number of these patients experience considerable difficulties turning around. These real life effects give the patient needed biofeedback signals for stabilization and safer motion.

It will be appreciated that the image is not restricted to tiled floors, and may include other geometric patterns, such as parallel stripes. In addition, other images may be generated, such as views from real life (i.e. outdoors in a park or the like). The image may be a virtual image, in which the outside world is blocked out, or it may be an augmented image, in which the image is superimposed onto the person's view of the real world.

Figure 3:
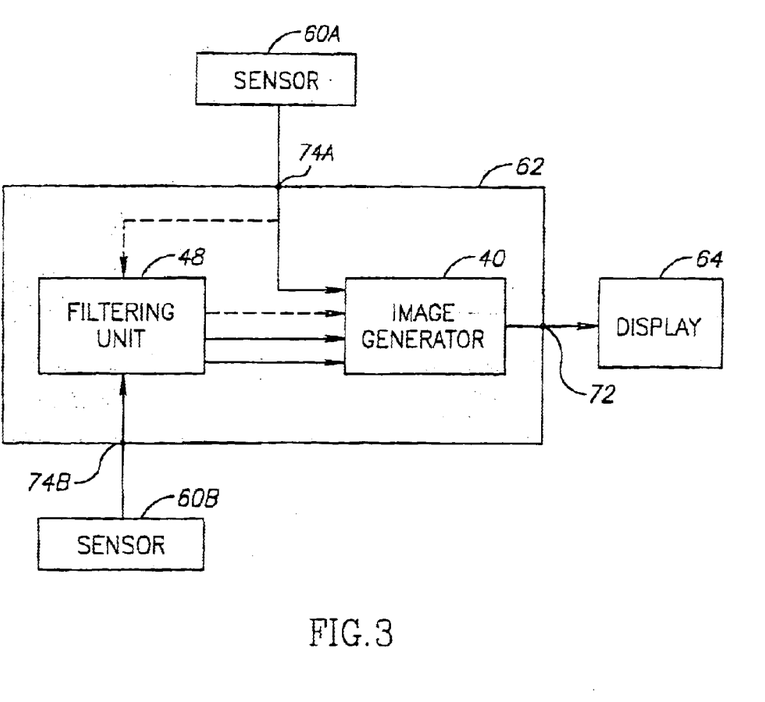
FIG. 3 is a block diagram illustration of a processor.

Reference is now made to FIG. 3, which shows details of processor 62 located within bodymounted assembly 54. Processor 62 may be a wearable computer or a microprocessor. Input data to processor 62 is obtained from sensors 60A and 60B at input ports 74A and 74B, respectively, and output data from processor 62 is sent to display 64 through output port 72.

Signals may be, but are not limited to, proportional direct current (DC), and indicate some motion parameter. For example, signals may contain acceleration data that is later converted to velocity data. Alternatively, signals may relate to an angle of head tilt, or other body movements. Signals from processor 62 to display 64 may be analog video signals, for example, PAL or NTSC, or they may be digital (e.g. VGA) signals. Conversion from analog to digital (A/D) or from digital to analog (D/A) may either be performed within processor 62, or external to processor 62 using a converter.

Processor 62 includes at least two components: a filtering unit 48, and an image generator 40. Filtering unit 48 filters signals received at input port 74B from sensor 60B. Signals from sensor 60A relating to movements other than head tilt may be filtered as well, as shown by dashed lines. Filtering eliminates unwanted components from the sensor signals, such as tremor, motor fluctuations and involuntary arm, leg and head movements, as described in further detail below. Image generator 40 then incorporates filtered data, as well as signals received directly from sensor 60A at input port 74A, and translates the received and filtered proportional signals into rates and degrees of motion of the displayed virtual floor. Image generator 40 then adapts the base image (such as the one shown in FIG. 2A) according to the generated rate and degree of motion information. Adapted images are sent through output port 72 to display 64 to be viewed by the user.

Figure 4:
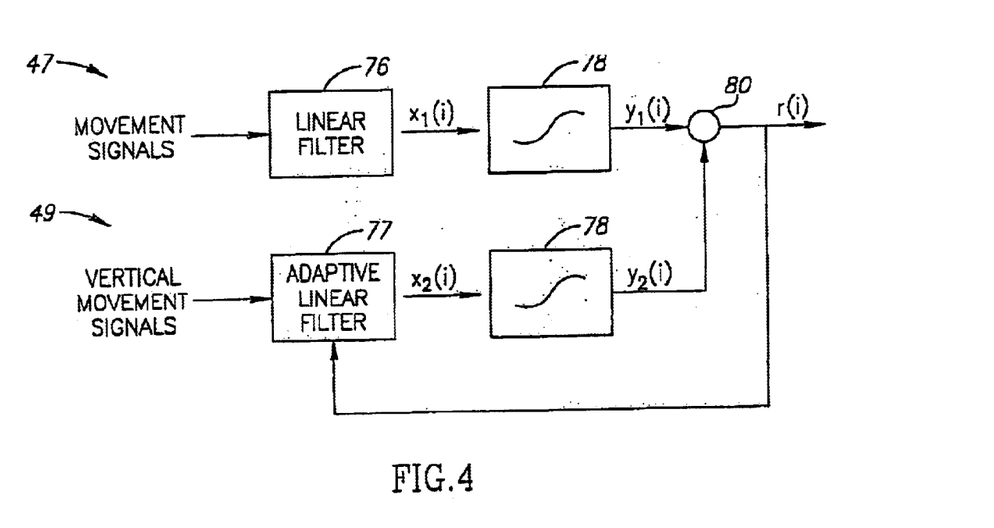
FIG. 4 is a block diagram illustration of one component of the processor of FIG. 3 in greater detail.

Reference is now made to FIG. 4, which is a block diagram illustration of a filtering component 45 of filtering unit 48, used for filtering tremor, and other unwanted motions. Each filtering component 45 in filtering unit 48 is used for filtering signals related to motion in one particular axis or direction. Thus, filtering unit 48 may have one or several filtering components 45, depending on the number of axes of movement being measured.

First, noisy sensor data are generally cleaned by filtering. Signals relating to vertical movement (up/down), representing tremor and other involuntary movements, are then subtracted from signals relating to translational movement (forward/back or side/side) or other voluntary movements. In this way, both noise from signals and unwanted motions and tremor are filtered out.

Filtering unit 48 has an upper path 47 and a lower path 49. Upper path 47 is used for cleaning signals from voluntary movement. This may include translational, rotational, or other movements, which may be measured, for example, using a 3-axis accelerometer. Lower path 49 is used for eliminating tremor and involuntary movement, based on receipt of vertical (up/down) movements. Vertical movements may also be obtained from a 3-axis accelerometer, or by other measuring means.

In upper path 47, a linear filtering element 76 is used to clean signals in one axis, for example, forward acceleration, from voluntary movement or another voluntary movement in one axis, for example, forward acceleration. Output is related to input by the following equation: $x_1(i)=\Sigma a_k v_1(i-k)$ for k=1 ... K, where $v_1(i)$ and $x_1(i)$ are the input and output to linear filtering element 76 at time i, respectively, and $a_k$ are weights.

In lower path 49, an adaptive linear filtering element 77 is used. Adaptive linear filtering element 77 is, for example, 5-dimensional, and is similar to one proposed by Widrow B. and Winter R for a linear adapter noise canceller in "Neural nets for adaptive filtering and adaptive pattern recognition", Computer 21(3): p. 25, 1988, incorporated herein by reference in its entirety. Similar to linear filtering element 76, output is related to input by the following equation: $x_2(i)=\Sigma b_k v_2(i-k)$ for k=1 ... K, where $v_2(i)$ and $x_2(i)$ are the input and output to adaptive linear filtering element 77 at time i, respectively. However, as opposed to the linear filtering element 76, the $b_k$ are variable weights. K was taken to be 5, but can be any number.

Linear filter 76 and adaptive linear filtering element 77 both feed into sigmoidal elements 78. For sigmoidal elements 78, new outputs $y_1(i)$ and $y_2(i)$ are related to inputs $x_1(i)$ and $x_2(i)$ from linear filtering element 76 and adaptive linear filtering element 77, respectively by the following equation: $y_n(i)=\tanh(x_n(i))$ at time i. Since the sigmoidal function is bound between two predetermined values, the sigmoidal elements attenuate high-amplitude accelerations, which was found to improve performance over the use of linear elements alone. Any combination of linear and sigmoidal elements may be used. For example, the sigmoidal elements may be included in either upper path 47 or lower path 49, or both or neither.

In summer 80, output $y_2(i)$ from adaptive linear filtering element 77 is subtracted from output $y_1(i)$ from linear filtering element 76 to obtain a final output r(i). Weighs $b_k$ in adaptive linear filter 77 are then adjusted so as to minimize the squared final output $r^2(i)$.

It should be noted that by adapting the filtering process in this way, filtering unit 48 "learns" the user's motions. Filtering unit 48 may be considered a neural network.

Each axis of movement (forward/back or side/side, for example) uses its own filtering component 45. For each filtering component 45, the cleaned signal is sent from filtering unit 48 to image generator 40. Thus, image generator 40 may simultaneously obtain multiple filtered signals from filtering unit 48, as well as signals directly from sensor 60A, such as a tilt sensor.

Figure 5:
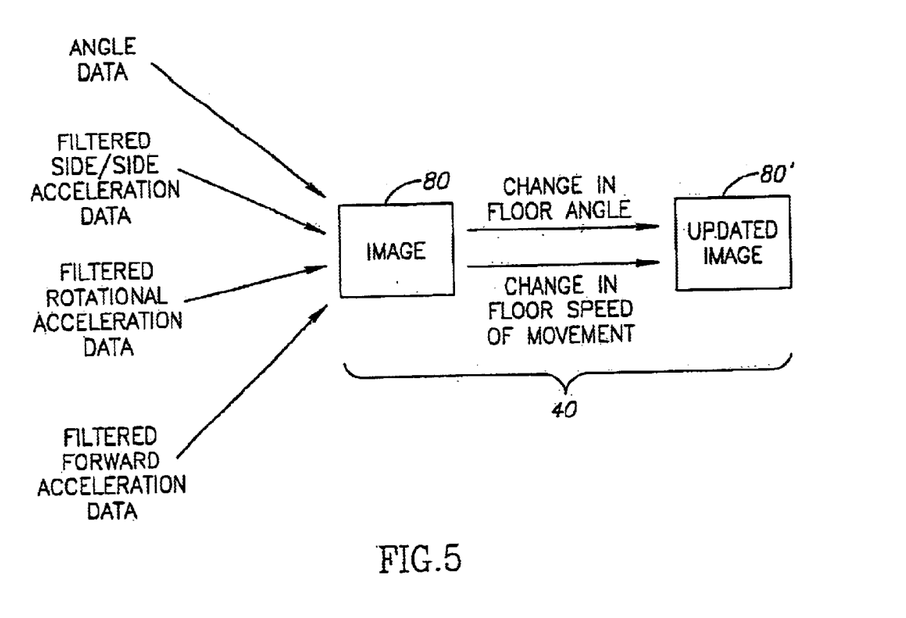
FIG. 5 is a block diagram illustration of another component of the processor of FIG. 3 in greater detail.

Reference is now made to FIG. 5, which is a block diagram illustration of image generator 40, used for creating images and adapting the images based on received filtered data. Specifically, an initial image 80 of a tiled floor, or other image, is created using an imaging software package (OpenGL™, Silicon Graphics, Inc., Mountain View, Calif., USA). Data from sensors, which may be filtered or unfiltered, are fed into image generator 40, and are used to make corresponding proportional changes in floor angle and speed of movement of image 80, resulting in an updated image 80', also provided by the imaging software. In the case of acceleration data, the filtered acceleration signals are converted into rate of motion data within image generator 40, typically using an integrator.

Thus, the tilt angle received from sensor 60A, is translated into an inclination angle of the virtual tiled floor so as to create a realistic view of the floor. Tripping or falling motions result in larger angles, and are translated into a proportional outward expansion of image 80, as in real-life vision.

Sensors 60A and 60B may also detect turning motions, which are translated into counter-turning motions of the virtual floor.

The rates of motion of the virtual tiled floor are the same as the rates of body motion of the user, occurring in opposite directions so as to create the sensation of a floor fixed in space. The tilt of the virtual floor is the same as that of the user's head, as measured by head-mounted sensor 60A. Parameters such as tile size, color and intensity of the virtual floor are adjustable.

Because of filtering unit 48, a forward motion of the tiled floor will not be triggered by leg tremor, and expansion of tile images, indicating a stumble or a fall, will not be caused by head tremor. Learning and filtering are performed on-line, as the patient's dynamic characteristics keep changing in time.

The present invention may potentially be used for anything that other virtual reality devices are used for, such as entertainment, industry, science and medicine. The use of accelerometers allows for free movement and is not restricted by location or space. In addition, it allows for adaptation of the image to full body motions. Thus, for example, one embodiment of the invention may include a device which would enable a sport or any other recreational activity (i.e. sexual activity) to be performed with a virtual background scene, outside of an entertainment room allowing for more body movements. In another embodiment, the device could be connected to the Internet, allowing for direct interaction between patients and doctors or between users. Movement disorders may include stroke, trauma, PD, or other central nervous system disorders and degenerative diseases. Also, it may include birth defects and results of aging.

EXPERIMENTAL DETAILS SECTION

A prototype of the proposed invention has been developed and systematically tested on PD patients supervised by a team of medical doctors in the Movement Disorders Clinic at the Cognitive Neurology Department of the RAMBAM Medical Center in Haifa, Israel.

Figure 6:
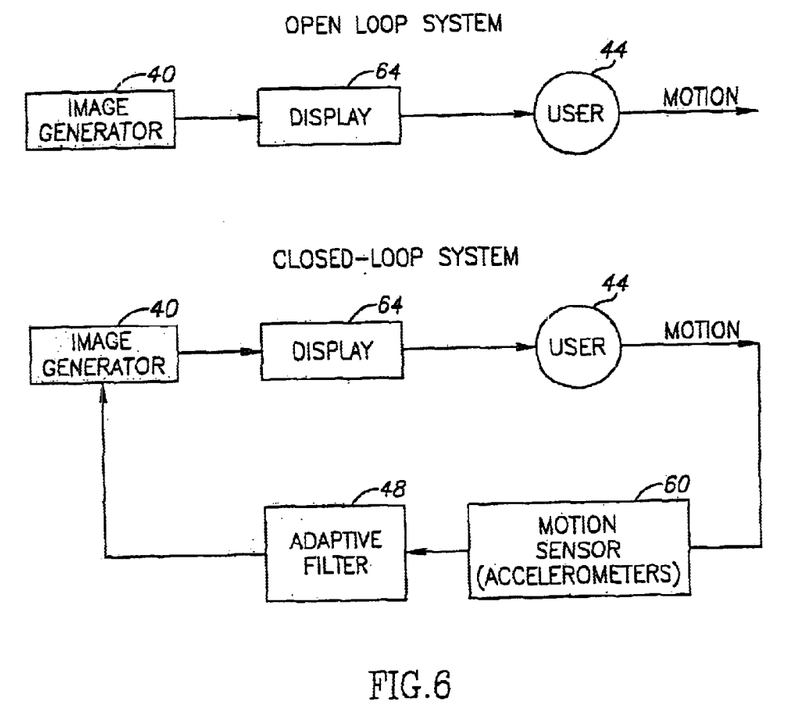
FIG. 6 is a block diagram illustration of open-loop and closed-loop control.

Reference is now made to FIG. 6, which illustrates the concept of open-loop versus closed-loop control. In an open-loop system, an image generator 40 produces a display 64 for a user 44 to see. User 44 may then react to display 64, and voluntarily begin to move. This, however, has no effect on image generator 40. In a closed-loop system, the motion of user 44 is sensed by motion sensors 60, which send signals related to this motion through a filtering unit 48 and back to image generator 40. In contrast to the open-loop system, which does not measure or respond to the body motions of user 44, the closed-loop system incorporates signals from motion sensors 60 into display 64.

Figure 7:
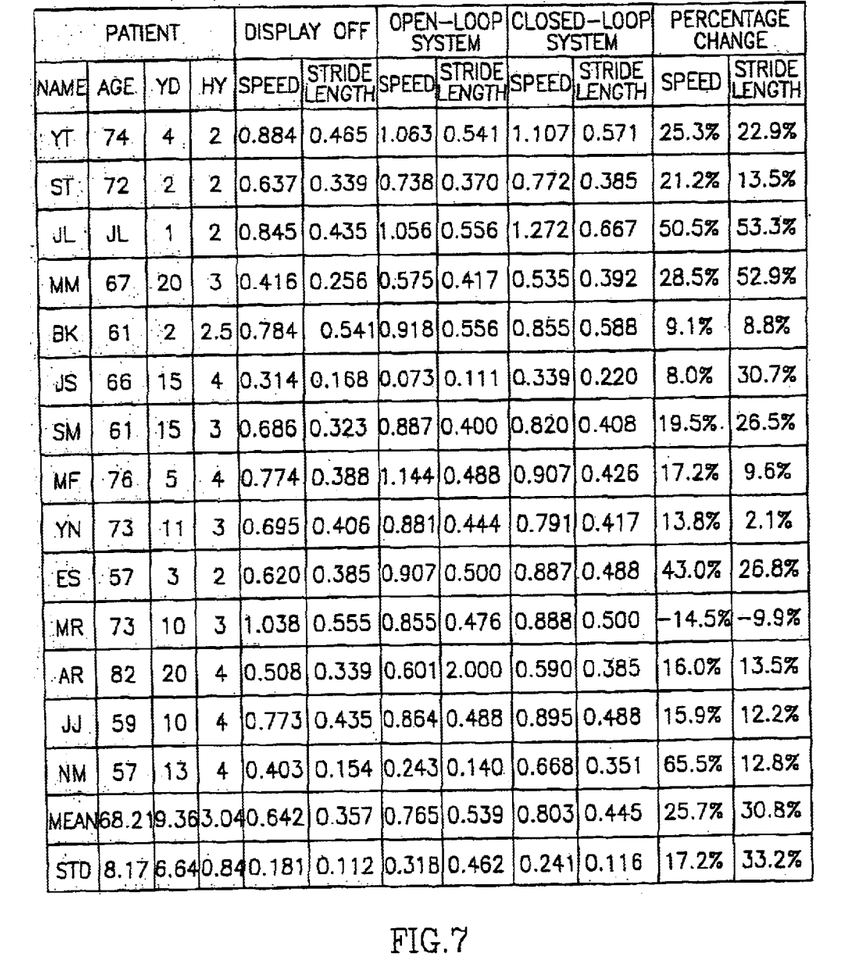
FIG. 7 is a table showing results from tests performed using one embodiment of the present invention.

Reference is now made to FIG. 7, which is a table showing details about the subjects who participated in the study, and the results obtained with the display off, with open-loop display, and with closed-loop display. For open-loop display, no sensors were activated on the subject for measuring movements, resulting in an image displayed at a predetermined speed towards the observer. Speed and stride length are listed for each test per subject, and the final two columns list a percentage change for the tested parameters.

Fourteen subjects, all clinically diagnosed with idiopathic PD and treated with Dopaminergic medication, participated in the study. The subjects' initials, ages, number of years having the disease (yd) and disease severity on the Hoehn and Yahr (HY) scale (See Hoehn M M and Yahr M D: "Parkinsonism: onset, progression and mortality." Neurology 17(5):427–42, 1967) are listed in FIG. 7. All subjects had 20/20 visual acuity, with correction when necessary. The tests were always performed at approximately the same time of day, and either following a 12-hour period without medication, or during the "off" state of the disease, which is characterized by severe immobility.

Each test consisted of a subject walking a stretch of 10 meters 4 times. Only results from the last two out of four tests in each category were used, to eliminate the effect of training. At the start of each test, the subject was verbally instructed to start walking. The length of time and the number of steps to completion of the 10-meter stretch were recorded for each test. Speed in meters/second (m/s) and stride length in meters (m) were calculated. In the first test (the reference test) the display was turned off. In the second, the open-loop system was turned on, displaying a virtual tiled floor in perpetual motion towards the observer at the maximal speed level comfortable for the subject. The third test employed the adaptive closed-loop system. The order of the second and the third tests was then reversed and results were averaged, in order to eliminate the effect of training from the comparison.

The last two columns of FIG. 7 list the percentage changes in the performance parameters obtained for the closed-loop system with respect to the reference test. It can be seen that, in all cases but one, performance was improved significantly with respect to the reference test when the closed-loop system was turned on (higher speed, longer strides).

Qualitative results were noted by the testers as well. Improvement in the quality of the steps was observed. Subjects who dragged their feet on the ground in the reference test raised them noticeably higher when the closed-loop system was turned on. Improvement was particularly dramatic in subjects tested during their "off" phase (JS and NM), characterized by severe immobility. These subjects were severely Brady-kinetic, unable to stand or start walking on their own. When the closed-loop display was turned on, and the subjects were instructed to watch the display, both subjects were able to start walking unaided. The one subject who did not benefit from the closed-loop system, MR, had no walking impairment; as can be seen from his test parameters, he had the best performance during the reference test.

Comparison of results for the open-loop system and the closed-loop system shows that the average values are similar. However, the standard deviations for the open-loop system are much higher than for the closed-loop system as well as the reference test. This means that the open-loop system affects different individuals in very different ways. The behaviors of JS and NM are particularly noteworthy in this respect. Both subjects improved their performance parameters with respect to the reference test when the closed-loop system was turned on, and both experienced freezing episodes when the perpetual motion display (open-loop system) was turned on. For both subjects, the performance parameters for the open-loop system are even lower than for the reference test. Some subjects reported discomfort, dizziness and nausea caused by the perpetual floor motion of the open-loop system. Most subjects reported relative comfort with the self-activated, closed-loop adaptive system and indicated a clear preference for it over the open-loop system.

The last two rows in the table show the average performance of the subject group (excluding MR, who, as noted before, had non-gait related impairment). It can be seen that, on average, the proposed closed-loop system improves performance by about 25% (speed) or 30% (stride length) with respect to the reference test. It should also be noted, however, that the standard deviations of these results are rather high, which implies that the results should be evaluated mainly on an individual basis. Certain PD patients would be helped by the proposed approach to a very significant degree (50%–100%), while others would be helped to a lesser degree. Few, in particular those without walking impairments, would not be helped at all.

Similar tests done on non-PD patients, such as stroke victims, have shown similar improvements in the walking abilities of these patients using the apparatus as described hereinabove.

Our study is the first to show the benefit of augmented reality, adapted to a person's own motion, for gait control in PD patients. In particular, we have shown the advantage of a closed-loop adaptive display of a virtual tiled floor as compared to a previously proposed open-loop, non-adaptive, perpetual virtual motion display. Our experiments have shown that adaptive augmented reality can significantly improve the walking abilities of most PD patients without causing the discomfort and the freezing phenomena associated with the open-loop system.

Finally, it is important to note that the gait parameters most affected by the proposed approach, namely, speed and stride length, also respond, to a similar extent, to antiparkinson medication (See Pedersen S W, Eriksson T and Oberg B: "Effects of withdrawal of antiparkinson medication on gait and clinical score in the Parkinson patient", Acta Neurol. Scand. 84, 7, 1991) as well as to pallidotomy (brain surgery), as reported by Siegel K L and Metman L V: "Effects of bilateral posteroventral pallidotomy on gait in subjects with Parkinson's disease". Arch. Neurol.,57, 198, 2000. However, medication causes involuntary movement which disturbs gait further.

The proposed approach may make it possible to reduce medication and postpone surgical intervention. The proposed invention may be useful as treatment, as therapy, or as an assistive device.

It will be appreciated by persons skilled in the art that the present invention is not limited by what has been particularly shown and described hereinabove. Rather the scope of the invention is defined by the claims which follow:

What is claimed:

1. Apparatus for adaptive image generation, the apparatus comprising:
  at least one non-radiating sensor, mountable on a body, for detecting body movements and producing signals related to said body movements;
  a processor configured to receive said signals, said processor comprising
    a closed loop biofeedback adaptive filtering unit which filters tremors from said signals, thereby producing filtered signals, said filtering unit comprising at least one adaptive filtering element capable of learning and filtering tremors; and an image generator for providing filtered images from said filtered signals.

2. Apparatus as in claim 1 wherein said filtering unit comprises linear elements and non-linear elements.

3. Apparatus as in claim 1, wherein said filtering unit is a neural network.

4. Apparatus as in claim 1, wherein said at least one non-radiating sensor includes an accelerometer.

5. Apparatus as in claim 1, wherein said generated image includes a geometric pattern.

6. Apparatus as in claim 1, wherein said generated image includes a view from real life.

7. Apparatus for augmented reality, the apparatus comprising:

at least one sensor mountable on a body for producing signals from movements of said at least one part of a body;

a processor for adapting an augmented image based on said signals, said processor comprising a closed loop biofeedback adapting filtering unit which filters tremors from said signals, thereby producing filtered signals and comprising at least one adaptive filtering element capable of learning and filtering tremors; and an image generator for providing images from said filtered signals.

8. Apparatus as in claim 7, wherein said filtering unit comprises linear elements and non-linear elements.

9. Apparatus as in claim 7, wherein said filtering unit is a neural network.

10. Apparatus as in claim 7, wherein said at least one sensor includes an accelerometer.

11. Apparatus as in claim 7, wherein said virtual image includes a geometric pattern.

12. A system for adaptive augmented reality, the system comprising:

at least one non-radiating sensor, mountable on a body, for detecting body movements and producing signals related to said body movements;

a processor configured to receive said signals relating to said body movements, said processor comprising a closed loop biofeedback adaptive filtering unit which filters tremors from said received signals, thereby producing filtered signals and comprising at least one adaptive filtering element capable of learning and filtering tremors;

an image generator for providing images from said filtered signals; and a display for displaying said filtered images.

13. Apparatus as in claim 12, wherein said filtering unit comprises linear elements and non-linear elements.

14. Apparatus as in claim 12, wherein said filtering unit is a neural network.

15. A system as in claim 12, wherein said at least one non-radiating sensor includes an accelerometer.

16. A system as in claim 12, wherein said generated image includes a geometric pattern.

17. A system for adaptive virtual reality, the system comprising:

at least one non-radiating sensor, mountable on a body, for detecting body movements and producing signals related to said body movements;

a processor configured to receive said signals, said processor comprising a closed loop biofeedback adaptive filtering unit which filters tremors from said received signals, thereby producing filtered signals and comprising at least one adaptive filtering element capable of learning and filtering tremors;

an image generator for providing said images from said filtered signals; and a display for displaying said generated and adapted images.

18. Apparatus as in claim 17, wherein said filtering unit comprises linear elements and non-linear elements.

19. Apparatus as in claim 17, wherein said filtering unit is a neural network.

20. A system as in claim 17, wherein said at least one of said radiating sensors includes an accelerometer.

21. A system as in claim 17, wherein said generated image includes a geometric pattern.

22. A system as in claim 17, wherein said generated image includes a view from real life.

23. Apparatus for treating a movement disorder, the apparatus comprising:

at least one sensor, mountable on a body, for detecting body movements and producing signals related to said body movements;

a processor configured to receive said signals, said processor comprising a closed loop biofeedback adapting filtering unit which filters tremors from said received signals, thereby producing filtered signals, and further comprising at least one adaptive filtering element, capable of learning and filtering tremors; and an image generator for providing said generated and adapted images from said filtered and received signals.

24. Apparatus as in claim 23, wherein said filtering unit comprises linear elements and non-linear elements.

25. Apparatus as in claim 23, wherein said filtering unit is a neural network.

26. A system as in claim 23, wherein said at least one non-radiating sensor includes an accelerometer.

27. A system as in claim 23, wherein said movement disorder is Parkinson's disease.

28. A system as in claim 23, wherein said generated image includes a geometric pattern.

29. A system for reducing involuntary movement artifacts from a signal, the system comprising:

a voluntary movement processor for filtering a voluntary movement signal representative of a voluntary movement, said voluntary movement signal including involuntary movements therein;

an adaptive involuntary movement processor for adaptively filtering a vertical motion signal; and a subtractor for subtracting said involuntary movements from said voluntary movement signal to produce a reduced artifact signal, wherein said adaptive involuntary movement processor adapts its processing using said reduced artifact signal.

30. A system as in claim 29, wherein said involuntary movement includes tremor.

31. A system as in claim 29, wherein said voluntary movement includes walking.

32. A system as in claim 29, wherein said voluntary movement processor comprises linear and non-linear filtering elements.

33. A system as in claim 29, wherein said adaptive involuntary movement processor comprises linear and non-linear filtering elements.

34. A method for treating a movement disorder, the method comprising the steps of:

providing an image to a person with a movement disorder;

receiving at least one signals from said person;

filtering tremors from said at least one signal with a closed loop adaptive filter;

adapting said image based on said received and filtered at least one signal; and providing said adapted image to said person, wherein said adapted image enables said person to adjust body movements.

35. A method as in claim 34 wherein said image is a virtual image.

36. A method as in claim 34 wherein said image is an augmented image.

37. A method as in claim 34 wherein said step of filtering is accomplished using filtering unit comprising a closed loop adaptive filtering element.

38. A method as in claim 34 further comprising the step of measuring a walking parameter.

39. A method for reducing involuntary movement artifacts from a signal, the method comprising the steps of:

filtering voluntary movement signals representative of voluntary movements, said signals having involuntary movement artifacts, with a closed loop biofeedback adaptive filter;

filtering vertical motion signals representative of involuntary movements;

subtracting said filtered vertical motion signals from said filtered voluntary movement signals to produce a reduced artifact signal; and adapting said filtering of vertical motion signals using said reduced artifact signal.

\* \* \* \* \*